United States Patent [19]
Garito et al.

[11] Patent Number: 4,504,229
[45] Date of Patent: Mar. 12, 1985

[54] DENTAL PLACEMENT DEVICES AND METHODS

[76] Inventors: Jon C. Garito, 264 Hedge La., Hewlett Harbor, N.Y. 11577; Alan G. Ellman, 1 Auerbach La., Lawrence, N.Y. 11516

[21] Appl. No.: 458,147

[22] Filed: Jan. 14, 1983

Related U.S. Application Data

[63] Continuation-in-part of Ser. No. 282,942, Jul. 13, 1981, abandoned, and a continuation-in-part of Ser. No. 437,803, Oct. 29, 1982, abandoned.

[51] Int. Cl.³ .............................................. A61C 5/00
[52] U.S. Cl. .................................... 433/215; 433/225
[58] Field of Search ..................... 633/228, 229, 215; 128/155, 157, 171

[56] References Cited

U.S. PATENT DOCUMENTS

| | | | |
|---|---|---|---|
| 3,337,957 | 8/1967 | Reed | 433/215 |
| 3,508,544 | 4/1970 | Moore et al. | 128/157 |
| 4,384,854 | 5/1983 | Garfinkel | 433/225 |

OTHER PUBLICATIONS

"Clinical Transplantation in Dental Specialities" C. V. Mosby Company, Copyright 1980, see p. 216.

*Primary Examiner*—Robert Peshock

[57] ABSTRACT

A novel placement device used for temporarily holding flexible splinting material against tooth surfaces while bonding same to the teeth during a dental splinting procedure, and novel methods for carrying out the splinting procedures using monofilaments for drawing the splinting material into interproximal spaces. The monofilaments are also useful for bonding bridges or retainers to teeth. The splinting material can also be bonded over the tooth's biting surface.

17 Claims, 13 Drawing Figures

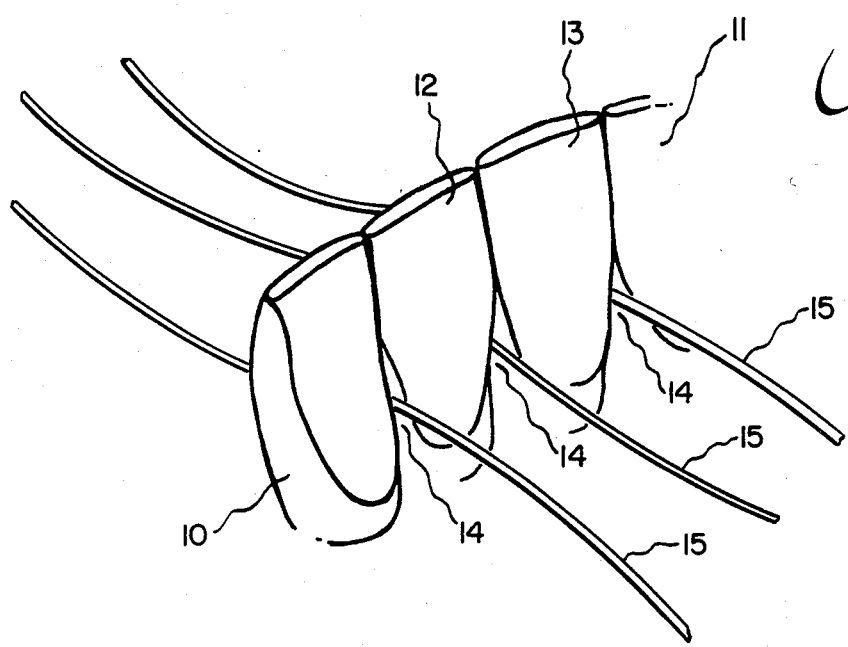
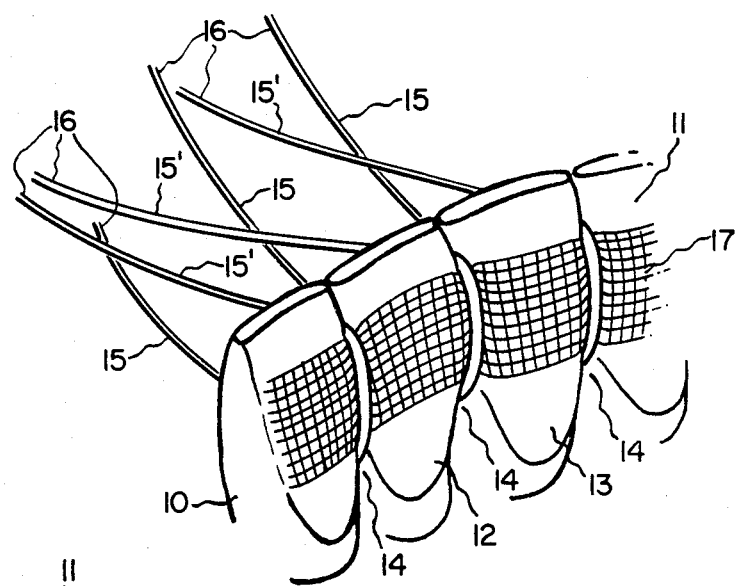
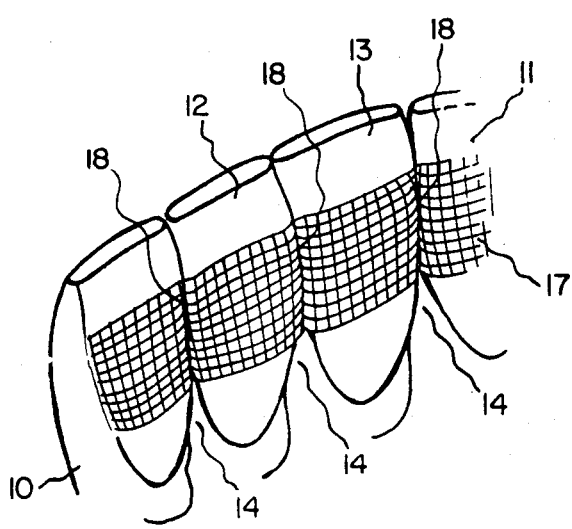

4,504,229

DENTAL PLACEMENT DEVICES AND METHODS

This application is a continuation-in-part of our prior copending application, Ser. No. 282,942, filed July 13, 1981 and now abandoned, and Ser. No. 437,803, filed Oct. 29, 1982 and now abandoned.

This invention relates to improved devices for placement of dental splints or retainers on a patient's teeth, and novel methods for dental splinting and application of bridge retainers.

BACKGROUND OF THE INVENTION

Recently different types of dental splinting devices and materials have become popular for stabilizing mobile or avulsed teeth. Some of these splinting materials include metal and plastic meshes, perforated metals, metal rods, bars, and the like. Our copending application, Ser. No. 282,942, describes some of these new splinting materials and the methods for applying them, the contents of which application are hereby incorporated by reference.

Problems have been experienced by dental practitioners in trying to adapt, place, handle and bond these splinting materials to tooth structure. An even greater problem arises when severe crowding of teeth exist making it difficult or impossible to place materials effectively and efficiently, and excessive time is consumed in such situations, as well as added discomfort for the patient and frustration to the dentist and his assistants.

A known placement device has been described, which is made of plastic provided with tabs and in which a slot is cut so that the placement material could be placed into the slot after application of the plastic to the teeth. This device is extremely complex in terms of fabrication of the plastic and requires careful slotting of thin plastic which is costly to manufacture. Furthermore, this prior art device requires careful placement into the slot of a strip of metal mesh which when pushed through often catches and the very fine mesh wires bend preventing the metal from being pushed through the slot. This often causes irreparable damage to the strip of metal, and great time loss to the dentist and patient. A further disadvantage of this prior art device is that the metal strip once placed through the plastic holder must be applied onto the segment of teeth to be splinted. To accomplish this, the plastic tabs must be slid along the metal strip. This often causes the metal mesh wires to catch again causing bending of the wires. Once the plastic holder is properly placed and resin bonded to the teeth, it is necessary to leave the plastic tabs in place. This is a significant disadvantage. It is impossible to remove the tabs without disturbing the embedded metal and resin.

In another dental procedure known as acid-etch bridge work or resin bonded retainer, a replacement tooth mounted on a retainer with bracket ears is placed by the dentist in the location where a tooth of the patient is missing, and the dentist holds the bracket ears against adjacent teeth while the bracket ears are bonded thereto. A problem is the difficulty of holding the small replacement tooth by hand or instruments while evenly applying pressure of the brackets against the tooth structure during hardening of the bonding material. Moreover, there is always concern about accidental dropping of the retainer and aspiration by the patient.

SUMMARY OF THE INVENTION

It is accordingly an object of the present invention to provide a novel placement device for simple placement of splinting materials to stabilize mobile teeth.

Another object of this invention is to provide a novel method of aligning splinting materials to the teeth.

Still another object is to provide a method of removing the placement device after the bonding material has hardened.

A further object is improved devices and methods for facilitating the placement and bonding of splinting materials, bridges, retainers and similar prosthetic devices.

Still a further object is improved splinting procedures to stabilize teeth individually as well as collectively.

Briefly stated, in accordance with one aspect of the invention, monofilament strips or its equivalent are used as the placement device. The strips are guided by the practitioner into the interproximal spaces of the segment of teeth to be immobilized, and are rested at the gingival portion. The splint is now placed on the lingual or buccal segments. The monofilaments are now brought over the splint and placed interproximally into the upper spaces, the ends are brought together and can be pulled or drawn as a draw string to tighten and bring or press the splint against the lingual or buccal segments to hold temporarily the splint against the teeth and to allow the splint to be brought into the interproximal section for additional bonding strength when the bonding material is applied as described in said copending application, Ser. No. 282,942.

A further advantage of this aspect of the invention is that, because the monofilaments are placed interproximally, the splint is automatically customized to the patient's tooth position and condition. Also, once the bonding material hardens with a splint covered or impregnated with the resin, the special monofiliments will not ahdere and will simply slip away from the hardened resin by releasing one end of the looped filiments and pulling.

In accordance with another aspect of the invention, a placement device is provided comprising plural monofilaments tied together at least at one end by a common strip. With this structure, after each of the free ends of the monofilaments have been inserted interproximally and the splint applied, the common strip can be manipulated as a unit for drawing the plural filaments together to press the splint against the teeth.

In accordance with still a further aspect of the invention, especially in a situation where a posterior tooth is missing, the monofilaments can be used to tie portions of the splint to the teeth present to secure same thereto prior to application of the bonding material, and can also be used interproximally to tie together splinting material provided on both facial and lingual surfaces of the teeth to be stabilized. This method increases the teeth surface area covered and thus the holding power of the splint to the teeth, greatly simplifying application of the bonding material and enhancing its bonding strength after hardening.

The above features have been described in our copending application, Ser. No. 437,803, the contents of which are hereby incorporated by reference.

In accordance with another aspect of the invention, which is applicable not only to splinting materials but also to bridges or retainers, the monofilament placement means are attached, as by tacking or threading, to the splint, bridge or retainer, so that the placement means can be used to support and position the latter in addition to pressing or pulling same against the patient's teeth after properly positioned during the bonding process. This further simplifies the involved dental procedure and reduces the possibility of accidental dropping of the prosthetic or stabilizing device.

In accordance with still another aspect of the invention, the splinting material is bonded over the incisal or biting surfaces of a tooth or teeth, and if necessary or desired subsequently adjusted to improve the shape of the biting surfaces. This offers the benefit of a relatively low cost procedure for reinforcing weakened incisal tooth edges, especially for brittle anterior teeth, without significantly compromising the patent's appearance.

BRIEF DESCRIPTION OF THE DRAWINGS

The invention will now be described in greater detail in connection with several examplary embodiments, reference being made to the accompanying drawings wherein:

FIG. 1 is a schematic view of several teeth showing a first step in accordance with a method of the invention;

FIG. 2 is a view similar to FIG. 1 of a further step of the method;

FIG. 3 is a view similar to FIG. 1 showing the splint in position after bonding at the conclusion of the procedure;

DETAILED DESCRIPTION OF PREFERRED EMBODIMENTS

Figure 4:
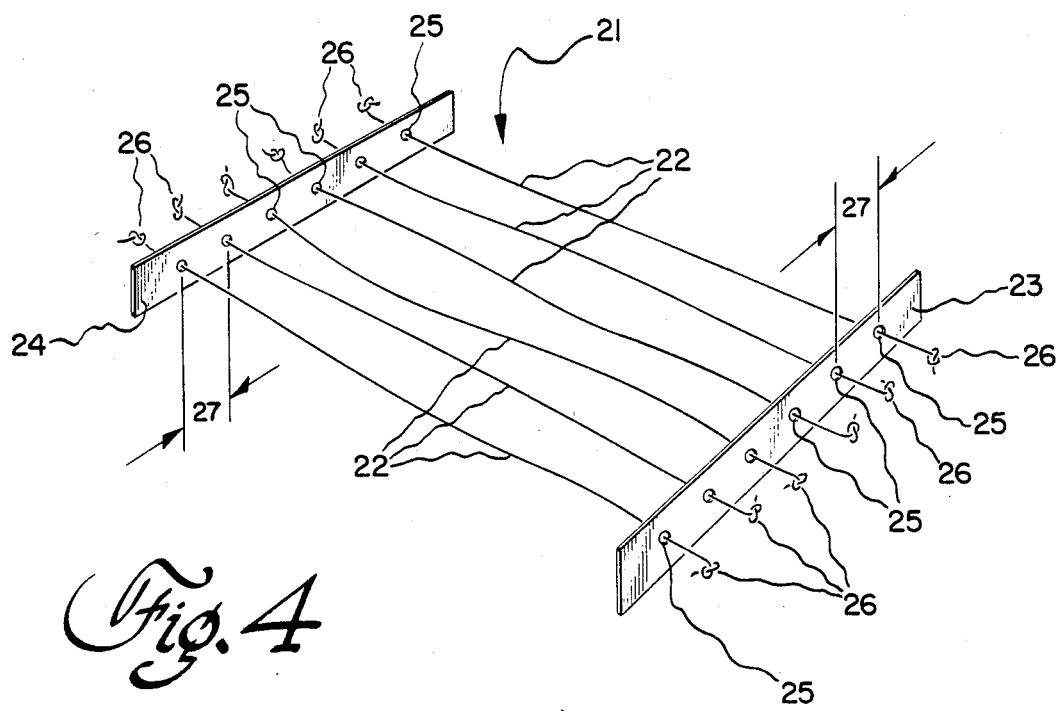
FIG. 4 is a schematic plan view of one form of placement device in accordance with the invention.

The invention is for use with many kinds of splinting materials which are of strip or rod configurations with or without perforations. The strip or thin rod should have sufficient flexibility that application of the placement device will cause the strip or rod to bend or flex and be pulled tight up against the tooth surfaces and into interproximal spaces. We prefer to use thin flexible perforated strips made of metal or plastic as described in our copending application, Ser. No. 282,942.

The bonding materials that can be employed in the invention can be chosen from among those currently available to dental practitioners for many uses in restorative dentistry. These are typically resin composites which are supplied by commercial dental suppliers in the form of pastes or creams, or in the form of powders when mixed with resin liquids form liquids, pastes or creams, which can be spread by the dentist over the splint and will selfharden usually by polymerization. Our said copending applications have several examples of hardenable resins and composites suitable for use in the present invention.

Though the monafilament can be constituted of a thin malleable wire, the monofilament preferably is constituted of a plastic resin, such as NYLON. Being non-stranded and a non-mesh avoids the problem of strand or mesh ends catching on the tooth or splint during interproximal insertion. Another advantage of a NYLON filament is that it will not adhere to the hardened bonding material, and thus can be removed after use. However, metal filaments, or filaments of another composition, can be substituted if desired. If the filament material does bond to the hardened bonding material, it can be left in place after snipping off the unbonded parts. Alternatively, a non-stick layer, such as VASELINE, can be applied to the filament to prevent adhesion.

Referring now to the drawings, FIG. 1 shows schematically a lingual view of a teeth segment to be splinted comprising four teeth of which, say, the two end teeth 10, 11 are immobile but the adjacent middle teeth 12, 13 are mobile and are to be stabilized by application of a splint. As depicted in FIG. 1, three monofilaments 15 are inserted in the interproximal spaces 14 and rested on the gingival tissue. Next, as depicted in FIG. 2, a flexible splinting mesh 17 is manually placed on the lingual surfaces across the teeth segment to be stabilized. Each of the filaments 15 are next reinserted interproximally, shown at 15', so as to loop over the mesh 17. The dentist or his assistant next collects the free ends of the filaments, designated 18, which protrude from the facial surfaces and pulls them taut, as plural draw strings can be drawn taut. This action temporarily presses the splinting mesh 17 against the teeth surfaces and pulls it into the interproximal spaces 14 as depicted in FIG. 2. Next, while still holding the filaments taut, composite bonding material (not shown) is spread over the mesh surface so as to fill the mesh interstices and to extend as a thin layer over the mesh edges and into the interproximal spaces 14 through the mesh interstices and around the mesh edges. This described in our copending application Ser. No. 282,942, and is not shown to avoid cluttering up the drawing. Then the composite is allowed to harden while still holding the filaments taut. Typically, this takes about 5 minutes. After hardening, if the filaments 15 have not adhered to the hardened composite, one end of each is released and the held end used to pull the filaments 15 out of the interproximal spaces 14. The final structure is the composite-stiffened mesh resin-bonded to and across the teeth and acting as a splint anchored on the immobile teeth 10, 11 to stabilize the mobile teeth 12, 13. This is illustated in FIG. 3, with again the resin omitted for clarity. This completes the procedure, except for any trimming of excess portions the splint or hardened composite as deemed necessary.

As will be evident from the preceding description, the method of the invention is simple to practice, consumes little time, and is less subject to the annoyances and frustrations of the known procedures. Increased bonding strength can be achieved, since the splinting mesh contacts more tooth surface and is reinforced by the splint portions, shown schematically at 18 in FIG. 3, extending into and bonded into the interproximal spaces 14. Moreover, the placement device, in this case the monofilaments, used to temporarily hold the splint against the teeth during bonding, is inexpensive and readily available, and can be disposed of after use.

FIG. 4 illustrates one form of novel placement device wherein plural filaments are united by a common strip portion to simplify manipulation of the placement device during the splinting procedure. As shown, the device, indicated generally by 21, comprises six monofilaments 22 joined or united at one end by a first common strip 23, preferably but not necessarily of the same material as the monofilaments 22, and also united at the opposite ends by a second common strip 24. In the form illustrated, which is exemplary only, the strips 23, 24 are of thin plastic sheet material provided with spaced holes 25, and the filaments 22 are each passed through the holes 25 as shown and knots 26 formed at their free ends to prevent the filaments from slipping back out of the holes. Alternatively, the filament ends could be bonded or otherwise secured to the strips. While only one common strip 23 or 24 can be used, we prefer to use common strips at both ends to simplify handling. While it is also possible for all filament ends at one side to come to a common point or juncture, we prefer that the ends of the monofilaments, which typically are 0.1-1 mm wide, where joined, are spaced apart by a distance, indicated at 27, approximating the interproximal spacing of, for example, 3-8 mm.

In use, the monofilaments are each inserted, one at a time, interproximally, in the same manner as dental floss while the dentist holds the filaments 22 taut by pulling on the end strips 23, 24, generally as depicted in FIG. 1; next the splint in applied; then one common strip, say 23, is used to loop the plural filaments 22 over the splint and back into the interproximal spaces, as depicted in FIG. 2. Then the common handling strips 23, 24 are pulled and held and the procedure continued as above described. To remove the filaments after bonding, one common strip is snipped off and the other strip used to pull the filaments out.

Single monofilaments can be employed in still another beneficial manner in accordance with another aspect of the invention. A condition occasionally encountered is when a posterior tooth is missing. The lack of lateral support for adjacent teeth can, in time, result in loss of stability. A useful procedure is to splint across the gap to stabilize adjacent teeth as a permanent solution, or as is more common as a temporary expedient while a replacement tooth is being fabricated for mounting in the empty space. For permanent splinting, horizontal grooves are often ground along the facial or lingual surfaces for receiving a rigid splint bar which after bonding permanently stabilizes the situation. However, this is not very useful as a temporary measure since, when the rigid splint bar is removed, the grooves remain as permanent tooth damage.

Figure 5:
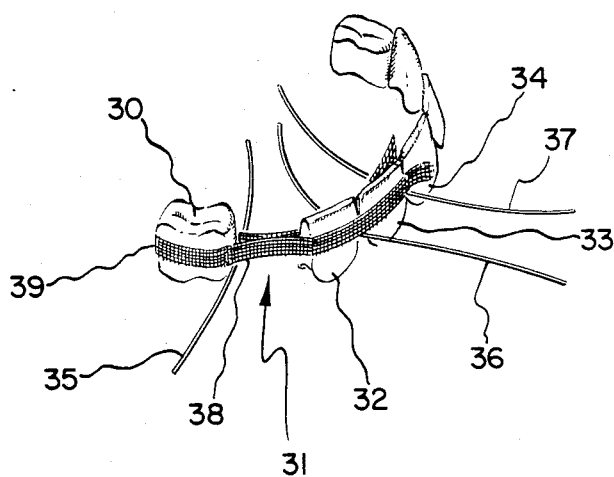
FIG. 5 is a schematic view of posterior teeth illustrating an early step in a method in accordance with another aspect of the invention.
Figure 6:
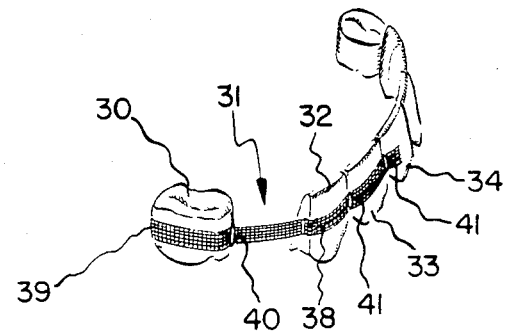
FIG. 6 is a view similar to FIG. 5 of a later step in that method.

In accordance with this aspect of the invention, a flexible splinting material of the type above described can be employed as a temporary splint. The problem is how to anchor adequately the flexible splint to the adjacent posterior teeth without physically damaging them and in a manner which will allow removal of the splint when the permanent tooth is to be mounted. One suitable method is depicted in FIG. 5, which shows an isolated posterior tooth 30 separated by space 31 from a row of adjacent teeth 32, 33, 34. Monofilaments 35, 36, 37 are inserted as shown and rested on the gingival tissue. Next, a long thin flexible splinting material 38 formed as a ribbon or band is wrapped as shown with its medial portion 39 carried around the distal of the distal tooth 30 of the segment to be splinted, and with the buccal and lingual ribbon ends extending along the corresponding teeth surface. Now the first filament 35 is ligated 40 (tied) around the buccal and lingual, overlying, ribbon portions, along the mesial surface of the isolated tooth 30, and the remaining filaments 36, 37 are ligated 41 over both adjacent ribbon portions, and the free ends snipped off, as depicted in FIG. 6. This secures the ribbon splint to the teeth and in each interproximal space and presses the ribbon up against the teeth surfaces as in the previous embodiments. The free ends of the splint ribbon can be finished off into an interproximal space. Next, which is not illustrated, the composite is spread over the ribbon to impregnate same and over adjacent tooth surfaces as before, and allowed to harden, stiffening the ribbon and bonding same to the abutting teeth. This will adequately stabilize the teeth as a temporary measure pending replacement of the missing tooth. An important advantage of this procedure is that the temporary splint is easily removed by grinding or the like leaving the basic teeth structure in undamaged condition.

In the previous embodiments described, the monofilament placement device was separated from the splint. FIGS. 7-10 illustrate modifications in which the monofilaments are attached to the splint and can perform not only the function of pressing the splint against the teeth during bonding, but also the function of supporting the splint during processing within the patient's mouth or external thereto. This offers the benefits of facilitating handling of the splint, especially if it contains a layer of tacky bonding material, and also reduces the possibility that the loose splint or loose monofilaments may be accidentally dropped while working in the patient's mouth and thus accidentally aspirated by the patient.

Figure 7:
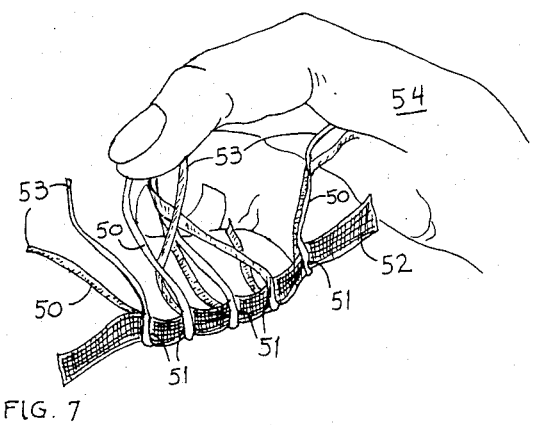
FIG. 7 illustrates a splinting procedure using monofilaments tacked to the splinting material in accordance with another aspect of the invention.
Figure 8:
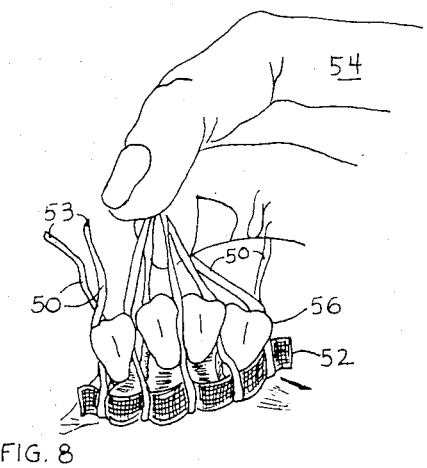
FIG. 8 illustrates a later step in the procedure of FIG. 7.

In the FIG. 7 embodiment, the plural monofilaments 50 have been tacked at medical locations 51 to a mesh-type malleable splint strip 52. By tacking is meant spot bonding using a drop of adhesive between the filament and splint regions tacked together. The splint 52 is now easily manageable by means of the loose filament ends 53. FIG. 7 illustrates one or more of the loose ends being handheld by the practitioner 54. In one preferred procedure for use with a study model, the splint would first be fitted to the model of the patient's teeth, for example, to trim to the desired length and width and to locate and make any desired V-notches as described in our copending application, Ser. No. 282,942, over the interproximal areas. Next, the monofilaments are tacked on using, for example, a cyanoacrylate adhesive at the locations of the interproximal areas of the model. Then, the adjusted splint 52 would be carried to the patient's mouth by means of the attached filaments, and, after a layer of bonding material, liquid adhesive or creamy composite, were spread over the teeth or on the side of the splint, or on both, is positioned over the teeth segment 56 to be splinted, as illustrated in FIG. 8, the monofilaments inserted in the teeth interproximal areas, and then, as described above in connection with FIGS. 1-3, the filaments used to pull the splint 52 up against the teeth surfaces and into the interproximal areas and held in that position while the bonding material hardens. Additional bonding material can be applied to ensure that the mesh interstices are filled, and if necessary excess bonding material removed or spread evenly over the mesh and adjacent tooth surfaces to provide a smooth surface that would be less objectionable to the patient. The mesh impregnated with the hardened bonding material forms the rigid splint desired.

Figure 9:
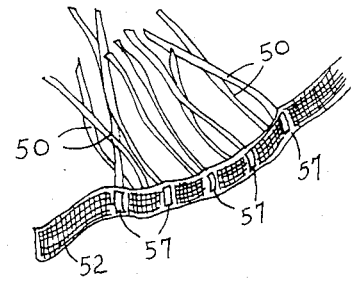
FIG. 9 shows a modification for the procedure of FIG. 7 employing monofilaments pre-threaded through a mesh-type splinting material.
Figure 10:
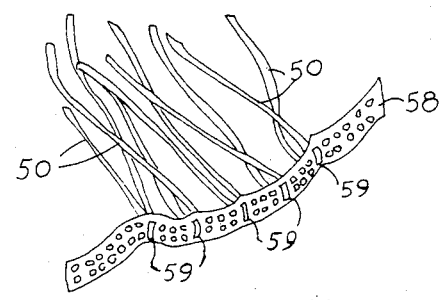
FIG. 10 shows a further modification employing monofilaments pre-threaded through a perforated band-type splint.

FIG. 9 illustrates a modification in which the monofilaments 50 are attached at the approximate interproximal areas by threading each of them through the mesh interstices as illustrated at 57. FIG. 10 shows a further modification in which the splint 58 is a perforated malleable strip of thin plastic or metal, and the monofilaments 50 are threaded through the perforations as shown at 59. After the splinting procedure is completed, excess filamentary material is removed by pulling (if the filament doesn't bond) or by snipping off the loose ends (if they do bond). The filament ends can be loose as depicted, or connected together at one or both ends by a tie strip similarly to that depicted in FIG. 4.

Figure 11:
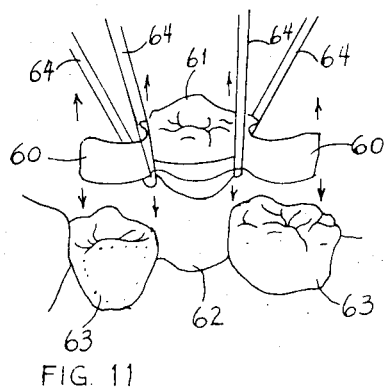
FIGS. 11 and 12 show modified procedures using tacked and pre-threaded monofilaments, respectively, for placement of a bridge or retainer.
Figure 12:
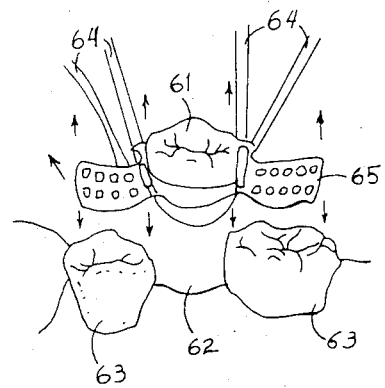

FIGS. 11 and 12 illustrate the inventive principle applied to a bridge or retainer of the "Maryland Bridge" type. The latter is constituted by a retainer of stiff brackets having outwardly extending ears 60 onto which a replacement tooth 61 is mounted. In the procedure, the bridge is lowered into place so that the replacement tooth fills the space 62 of a missing tooth, and while so hold the bracket ears 60 are secured as by bonding to the adjacent teeth 63. In the invention, monofilaments 64 are tacked to the bracket ears 60 and the monofilaments used to place the bridge in the correct position and to pull the bracket ears 60 against the adjacent teeth surfaces 63 while the bonding material hardens. In the FIG. 12 modification, the bracket ears 65 are perforated and the monofilaments 64 are threaded through the perforations as the means of attachment.

Figure 13:
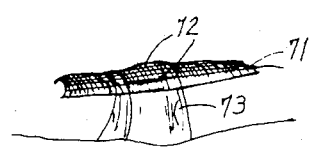
FIG. 13 shows part of a procedure in accordance with another aspect of the invention wherein the splinting material is bonded over the incisal edge of a tooth.

FIG. 13 illustrates another feature of the invention. In the splinting embodiments described herein and in our prior application, Ser. No. 282,942, the flexible splint strip is preferably bonded along the inner dental arch. The bonded strip, being thin with a smooth outer surface, is less visible in that position and causes less discomfort to the patient. However, for posterior teeth, where the splint would be less visible, it can be bonded along the outer dental arch. In this embodiment, the flexible splint strip, preferably of the metal mesh type, is bonded directly onto the bite surfaces or incisal edge of one or more teeth by means of the liquid adhesive or creamy composite. This is advantageous especially for restorative-perio splinting of weakened or brittle anterior teeth. This brittleness is critical for the incisal edge area of the tooth, which is thinnest and weakest, and thus this edge area is more easily broken while biting. This is a difficult problem to solve inexpensively. The inventive approach, which is very inexpensive, is to use the flexible or maleable elongated splint in its metal mesh form, and then bend or mold to a kind of slightly angled L-shape for one edge, or general U-shape for both edges, and then bond with the bonding material directly over the biting surface of the tooth, or across a row of plural adjacent teeth. This is illustrated in FIG. 13 which shows the bent molded strip 71 bonded over both biting edges 72 of one tooth 73. The impregnated bonded metal mesh strengthens or reinforces the incisal edges 72 and reduces the possibility of breakage. Following bonding, the excess mesh portions are trimmed off and the composite bonded mesh, now stiffened can be shaped by grinding or the like to improve cutting or biting efficiency of the tooth. Also, it may be necessary to grind down the matching teeth to attain a proper bite. But this technique, inexpensively, will protect the tooth and perhaps save it. Such low cost restoration procedures as this and the others described above means that proper dental care would be available to lower-income patients who can not afford the more expensive conventional restorations.

There has thus been described an improved placement device using single monofilaments or multiple-joined monofilaments to tamporarily hold a flexible splinting material or retainers against teeth surfaces prior to bonding the splint or retainer to the teeth. There has also been described improved methods using the monofilaments to temporarily anchor the splinting material to the teeth segment during application of the bonding material. As will be evident, the improved methods are simpler to use and will save valuable time of the dentist.

While our invention has been described in connection with specific embodiments thereof, those skilled in the art will recognize that various modifications are possible within the principles enunciated herein and thus the present invention is not to be limited to the specific embodiments disclosed.

What is claimed is:

1. A novel dental placement device for splinting a patient's teeth in combination with an elongated malleable splint strip having perforations and a length enabling the splint strip to be positioned along the dental arch so as to overlie end stable teeth and at least one intermediate mobile tooth and having a height perpendicular to its elongated direction enabling the splint strip to be located between the gingival tissue and the teeth biting surfaces, said placement device comprising multiple flexible monofilaments sized to fit interproximally of the patient's teeth without physically enlarging the interproximal spaces, said monofilaments having a surface constituted of a material to which bonding material will not adhere, median portions of each of the monofilaments being attached to spaced regions of the splint strip separated lengthwise along the splint strip by distances approximating the interproximal spaces between the patient's teeth where the splint is to be positioned, the orientation of each of the monofilaments being along the splint height such that the two free ends of each monofilament, when pulled taut in a direction transverse to the dental arch where the splint strip is to be positioned, will be located over and can be positioned in the same interproximal space with adjacent monofilaments being located over and positionable in adjacent interproximal spaces, whereby the splint strip can be supported by the ends of the monofilaments while positioning the splint strip on the patient's dental arch so as to overlie the said stable and immobile teeth, with the free ends of each monofilament located proximate to a different interproximal space so they can be placed in the same proximate interproximal space and used to pull and hold the splint strip against the patient's teeth and into the said interproximal spaces while bonding with bonding material the splint strip to the patient's teeth, a non-adhering character of the monofilament surface enabling removal of the monofilament from the interproximal spaces leaving only the splint strip bonded to and across the patient's teeth.

2. The combination as claimed in claim 1 wherein the monofilaments are of plastic and have a diameter of about 0.1–1 mm.

3. A novel dental placement device for replacing a missing patient's tooth in combination with a retainer for the replacement tooth having end bracket ears and a length enabling the retainer to be positioned along the dental arch with the replacement tooth overlying the missing tooth socket and with the bracket ears overlying adjacent teeth and having a height enabling the retainer to be located between the gingival tissue and the teeth biting surfaces, said placement device comprising multiple flexible monofilaments sized to fit interproximally of the patient's teeth without physically enlarging the interproximal spaces, said monofilaments having a surface constituted of a material to which bonding material will not adhere, median portions of each of the monofilaments being attached to one of the bracket ears separated by distances approximating the interproximal spaces between the patient's teeth including the replacement tooth where the latter is to be positioned, the orientation of each of the monofilaments along the retainer height being such that the two free ends of each monofilament, when pulled taut in a direction transverse to the dental arch where the retainer is to be positioned, will be located over and can be positioned in the same interproximal space with adjacent monofilaments being loacted over and positionable in adjacent interproximal spaces, whereby the retainer can be supported by the ends of the monofilaments while positioning the retainer on the patient's dental arch so that the replacement tooth is in the said socket and the bracket ears overlie adjacent teeth, with each monofilament located proximate to a different interproximal space so they can be placed in the same proximate interproximal space and used to pull and hold the brcket ears against the patient's teeth while bonding with bonding material the bracket ears to the patient's teeth, the nonadhering character of the monofilament surface enabling removal of the monofilaments from the interproximal spaces leaving only the retainer bonded to the patient's teeth and the replacement tooth in its socket.

4. The combination as claimed in claim 3 wherein the monofilaments are of plastic and have a diameter of about 0.1-1 mm.

5. The dental procedure of claim 1, wherein the splint strip or retainer has perforations, and the monofilaments are attached by threading same through the perforations.

6. The combination of claim 1 or claim 3, wherein the monofilaments are attached to the splint strip or retainer by being tacked to or threaded through the splint strip or retainer.

7. A novel dental procedure for reinforcing a patient's tooth, comprising the steps:
 (a) bonding a malleable mesh-type elongated strip onto and over the occlusial surface of the tooth,
 (b) thereafter trimming off excess strip sections extending beyond the occlusial surfaces,
 (c) thereafter adjusting the exposed bonded strip to enhance its biting function.

8. A dental procedure as claimed in claim 7 wherein the bonding step is carried out using a liquid or cream bonding material so as to cause the latter to spread through the mesh interstices, and smoothing the bonding material over the strip section overlying the occlusial surface.

9. A novel dental procedure for splinting a patient's teeth employing an elongated malleable splint strip having perforations and a length enabling the splint strip to be positioned along and bonded to the dental arch so as to overlie end stable teeth and at least one intermediate mobile tooth and having a height perpendicular to its elongated direction enabling the splint strip to be located between the gingival tissue and the teeth biting surfaces, comprising the steps:
 (a) providing as a placement device multiple flexible monofilaments sized to fit interproximally of the patient's teeth without physically enlarging the interproximal spaces, said monofilaments having a surface constituted of a material to which bonding material will not adhere,
 (b) attaching median portions of each of the monofilaments to spaced regions of the splint strip separated lengthwise along the splint strip by distances approximating the interproximal spaces between the patient's teeth where the splint is to be positioned, the orientation of each of the monofilaments being along the splint height such that the two free ends of each monofilament, when pulled taut in a direction transverse to the dental arch where the splint strip is to be positioned, will be located over and can be positioned in the same interproximal space with the free ends of adjacent monofilaments being located over and positionable in adjacent interproximal spaces,
 (c) supporting the splint strip by the ends of the monofilaments while positioning the splint strip on the patient's dental arch so as to overlie the said stable and immobile teeth, with each monofilament located proximate to a different interproximal space, and placing the two free ends of each monofilament in the same proximate interproximal space without physically enlarging same,
 (d) using the free ends of the monofilaments to pull and hold the splint strip against the patient's teeth and into the said interproximal spaces while bonding with bonding material the splint strip to the patient's teeth,
 (e) and thereafter separating the monofilaments from the splint strip and removing the monofilaments from the interproximal spaces leaving only the splint strip bonded to and across the patient's teeth.

10. A dental procedure as claimed in claim 9 wherein the monofilaments are of plastic and have a diameter of about 0.1-1 mm.

11. A novel dental procedure for replacing a missing patient's tooth employing a retainer for the replacement tooth having end bracket ears and a length enabling the retainer to be positioned along the dental arch with the replacement tooth overlying the missing tooth socket and with the bracket ears overlying adjacent teeth and having a height enabling the retainer to be located between the gingival tissue and the teeth biting surfaces, comprising the steps:
 (a) providing multiple flexible monofilaments sized to fit interproximally of the patient's teeth without physically enlarging the interproximal spaces, said monofilaments having a surface constituted of a material to which bonding material will not adhere,
 (b) attaching median portions of one of the monofilaments to each of the bracket ears separated by distances approximating the interproximal spaces between the patient's teeth including the replacement tooth where the latter is to be positioned, the orientation of each of the monofilaments along the retainer height being such that the two free ends of each monofilament, when pulled taut in a direction transverse to the dental arch where the retainer is to be positioned, will be located over and can be positioned in the same interproximal space with adjacent monofilaments being located over and positionable in adjacent interproximal spaces, (c) supporting the retainer by the ends of the monofilaments while positioning the retainer on the patient's dental arch so that the replacement tooth is in the said socket and the bracket ears overlie adjacent teeth, with each monofilament located proximate to a different interproximal space, and placing the two free ends of each monofilament in the same proximate interproximal space without physically enlarging the same, (d) using the free ends of the monofilaments to pull and hold the bracket ears against the patient's teeth while bonding with bonding material the said bracket ears to the patient's teeth, (e) and thereafter separating the monofilaments from the retainer and removing the monofilaments from the interproximal spaces leaving only the retainer bonded to the patient's teeth and the replacement tooth in its socket.

12. A dental procedure as claimed in claim 11 wherein the monofilaments are of plastic and have a diameter of about 0.1-1 mm.

13. A method of stabilizing teeth in a teeth segment comprising:

(a) inserting monofilaments, joined at opposite ends by common joining strips, interproximally of the teeth in the segment, (b) placing flexible splinting material across the teeth and the said interproximal spaces, (c) looping the monofilaments over the splinting material and back into the said interproximal spaces and pulling same so as to draw the splinting material into the said interproximal spaces, and (d) applying a hardenable bonding material over the splinting material while temporarily held by the monofilaments and allowing the bonding material to harden.

14. A novel dental procedure for splinting a patient's teeth employing an elongated flexible splint strip having perforations and a length enabling the splint strip to be positioned along the dental arch so as to overlie end stable teeth and at least one intermediate mobile tooth and having a height enabling the splint strip to be located between the gingival tissue and the teeth biting surfaces, comprising the steps:

(a) providing multiple flexible monofilaments sized to fit interproximally of the patient's teeth without physically enlarging the interproximal spaces, said monofilaments having a surface constituted of a material to which bonding material will not adhere, (b) inserting median portions of each of the monofilaments into the interproximal spaces between the patient's teeth where the splint is to be positioned, (c) placing the splint strip on the lingual side of the dental arch where the splint strip is to be bonded, (d) looping a free end of each monofilament over the splint strip and back into the same interproximal space where the other free end is located and then pulling on the free ends in a direction transverse to the dental arch so as to draw the splint strip up against the teeth lingual surfaces and into the said interproximal spaces, (e) applying a hardenable bonding material over the splint strip so as to penetrate the perforations while temporarily holding the splint strip by the monofilaments against the teeth surfaces until the bonding material hardens, (f) and thereafter removing the monofilaments from the interproximal spaces leaving only the splint strip bonded to and across the patient's teeth.

15. A dental procedure as claimed in claim 14, wherein the monofilaments are of plastic and have a thickness of between 0.1 and 1 mm.

16. A novel dental procedure for temporarily splinting a patient's teeth adjacent a missing tooth employing an elongated flexible splint strip having perforations and a length enabling the splint strip to be positioned along both sides of the dental arch so as to encircle one of end stable teeth and at least one intermediate empty tooth space to receive a replacement tooth and having a height enabling the splint strip to be located between the gingival tissue and the teeth biting surfaces, comprising the steps:

(a) providing multiple flexible monofilaments sized to fit interproximally of the patient's teeth without physically enlarging the interproximal spaces, said monofilaments having a surface constituted of a material to which bonding material will not adhere, (b) inserting median portions of each of the monofilaments into the interproximal spaces between the patient's teeth where the splint is to be positioned, (c) placing the splint strip on the lingual side of the dental arch where the splint strip is to be bonded and extending one portion of the strip around said one end stable tooth so as to extend over the facial side of said one tooth and over the said interproximal spaces from the facial side, (d) looping a free end of each monofilament over the splint strip and back into the same interproximal space where the other free end is located and then ligating each monofilament around adjacent splint strip portions so as to draw the splint strip up against the teeth lingual and facial surfaces and into the said interproximal spaces and into the empty space where the tooth is missing, (e) applying a hardenable bonding material over the splint strip so as to penetrate the perforations while the splint strip is held by the ligated monofilaments against the teeth surfaces and allowing the bonding material to harden providing temporary stabilization of the teeth until the replacement tooth is ready to be mounted.

17. A method as claimed in claim 16 wherein the monofilaments are of plastic and have a thickness of between 0.1 and 1 mm.

* * * * *

UNITED STATES PATENT AND TRADEMARK OFFICE
CERTIFICATE OF CORRECTION

PATENT NO. : 4,504,229

DATED : March 12, 1985

INVENTOR(S) : Jon C. Garito et al

It is certified that error appears in the above-identified patent and that said Letters Patent is hereby corrected as shown below:

Col. 9, line 40:

"claim 1" should read--claim 9 or claim 11--.

Signed and Sealed this

Twenty-third Day of July 1985

[SEAL]

Attest:

DONALD J. QUIGG

Attesting Officer    Acting Commissioner of Patents and Trademarks